United States Patent [19]
Kobayashi et al.

[11] Patent Number: 6,111,145
[45] Date of Patent: Aug. 29, 2000

[54] CYCLOPENTENONE DERIVATIVE

[75] Inventors: Eiji Kobayashi; Nobuto Koyama; Ikunoshin Kato, all of Otsu; Kaoru Inami, Ikeda; Tetsuo Shiba, Toyonaka, all of Japan

[73] Assignee: Takara Shuzo Company, Kyoto, Japan

[21] Appl. No.: 09/419,221

[22] Filed: Oct. 15, 1999

[30] Foreign Application Priority Data

Jun. 30, 1997 [JP] Japan .................................. 9-187205

[51] Int. Cl.$^7$ .................... C07C 49/105; A61K 31/12
[52] U.S. Cl. ................................. 568/379; 514/690
[58] Field of Search ................ 568/379; 514/690

[56] References Cited

U.S. PATENT DOCUMENTS

| | | | |
|---|---|---|---|
| 4,766,147 | 8/1988 | Noyori et al. | 514/530 |
| 5,149,711 | 9/1992 | Hazato et al. | 514/548 |
| 5,675,031 | 10/1997 | Furuya et al. | 560/53 |

FOREIGN PATENT DOCUMENTS

| | | |
|---|---|---|
| 1233255 | 9/1989 | Japan . |
| 2247151 | 2/1990 | Japan . |

OTHER PUBLICATIONS

Tajima et al, "Preparation of cyclopentenone derivatives as intermediates for pharmaceuticals and perfume", CA112:76456, 1990.

Carl R. Johnson, Bipin M. Nerurkar, Adam Golebiowski, Hari Sundram and John L. Esker, Chemoenzymatic Synthesis of trans–4,5–Dihydroxycyclopent–2–enones: Conversion to D–1–Deoxynojirimycin, *J. Chem. Soc., Chem. Commun.*, 1995, pp. 1139–1140.

International Search Report for International Application No. PCT/JP98/02516, Aug. 31, 1998.

*Primary Examiner*—Deborah C. Lambkin
*Attorney, Agent, or Firm*—Kolisch Hartwell Dickinson McCormack & Heuser

[57] ABSTRACT

A cyclopentenone derivative represented by the following formula [I] or an optically active substance or a salt thereof.

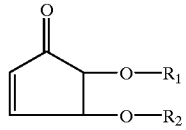

[I]

(In the formula, $R_1$ and $R_2$ are same or different and each of them is straight or branched alkyl group, straight or branched alkenyl group, aromatic group, aromatic-aliphatic group or H with a proviso that the case where $R_1=R_2=H$, or $R_1$=benzyl group and $R_2$=H is excluded.)

8 Claims, 9 Drawing Sheets

CYCLOPENTENONE DERIVATIVE

TECHNICAL FIELD

The present invention relates to the cyclopentenone derivative useful in the field of pharmaceutical agents having a physiological activity such as anticancer action and also relates to a method for the manufacture of said compounds.

PRIOR ART

Pharmaceutical agents which have been used in clinical therapy include many agents such as anticancer agents, antibiotic substances, immunopotentiators, immunomodulators, etc. (such as alkylating agents, antimetabolites and plant alkaloids) but it can be hardly said that such a drug therapy has been completely established already.

Among those agents, prostaglandin A and J having an α, β-unsaturated carbonyl in a five-membered ring among the prostaglandins derived from natural substances have been reported to have a possibility of being used as highly safe anticancer agents due to their inhibition of DNA synthesis and various derivatives of them have been synthesized (refer to the Japanese Laid-Open Patent Publication Sho-62/96438).

PROBLEMS TO BE SOLVED BY THE INVENTION

An object of the present invention is to develop the cyclopentenone derivative having a physiological action such as anticancer action, etc. and to offer a method for the manufacture of said compounds and pharmaceutical agents containing said compounds.

MEANS TO SOLVE THE PROBLEMS

The present inventors have conducted an intensive study for achieving said object and have found that the cyclopentenone derivative represented by the formula [II] is produced by the reaction of 4,5-dihydroxy-2-cyclopenten-1-one (hereinafter, referred to as just "cyclopentenone") represented by the formula [III] with alcohol and/or reactive derivative thereof and that said cyclopentenone derivative of the present invention has various strong physiological activity such as cell growth inhibiting activity on cancer cells, etc. whereby the present invention has been achieved.

The present invention will be summarized to be as follows. Thus, the first feature of the present invention relates to a cyclopentenone derivative represented by the following formula [I] or an optically active substance or a salt thereof.

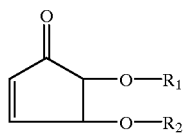

[I]

(In the formula, $R_1$ and $R_2$ are same or different and each of them is straight or branched alkyl group, straight or branched alkenyl group, aromatic group, aromatic-aliphatic group or H with a proviso that the case where $R_1=R_2=H$, or $R_1$=benzyl group and $R_2$=H is excluded.)

The second feature of the present invention relates to a method for the manufacture of a cyclopentenone derivative represented by the formula [II], characterized in that, 4,5-dihydroxy-2-cyclopenten-1-one represented by the following formula [III] and/or an optically active derivative thereof are/is made to react with alcohol and/or reactive derivative thereof corresponding to $R_3$ and $R_4$ of the cyclopentenone derivative represented by the following formula [II] either simultaneously or successively.

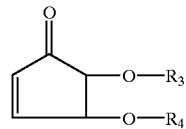

[II]

(In the formula, $R_3$ and $R_4$ are same or different and each of them is straight or branched alkyl group, straight or branched alkenyl group, aromatic group, aromatic-aliphatic group or H with a proviso that the case where $R_3=R_4=H$ is excluded.)

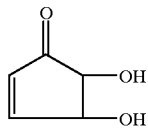

[III]

The third feature of the present invention is a pharmaceutical agent which is characterized in containing the compound selected from the cyclopentenone derivative, an optically active substance or a salt thereof of the first feature of the present invention as an effective component.

The fourth feature of the present invention is a pharmaceutical agent which is characterized in containing compound selected from cyclopentenone derivative, an optically active substance or a salt thereof obtained by the method of the second feature of the present invention as an effective component.

In a preferred embodiment of the third and fourth features of the present invention, said pharmaceutical agent is an anticancer agent, apoptosis inducer or antibacterial agent.

EMBODIMENTS OF THE INVENTION

Figure 1:
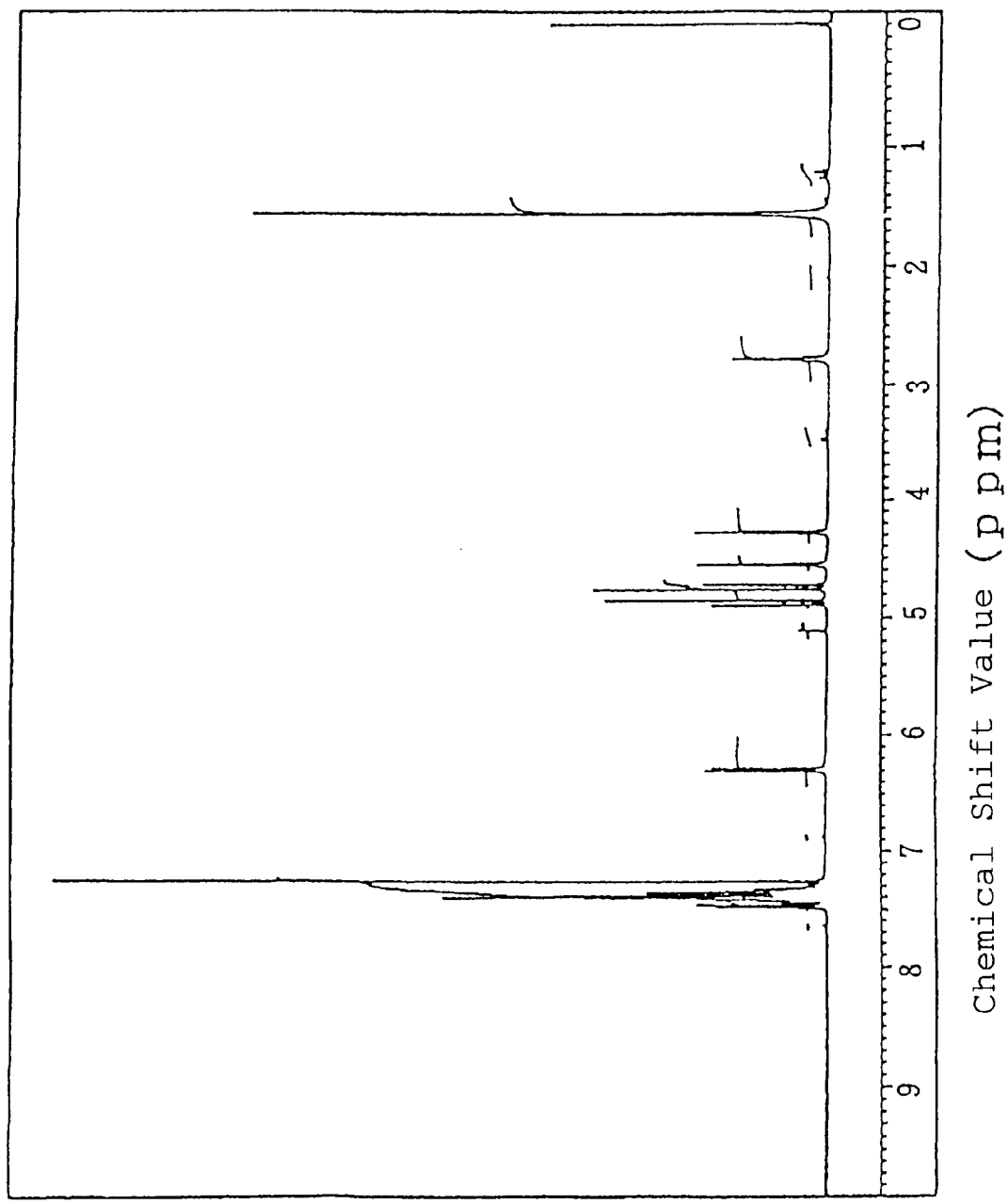
FIG. 1 shows a $^1$H-NMR spectrum of 4-benzylcyclopentenone ether.

The present invention will now be specifically illustrated as hereinafter.

The cyclopentenone represented by the formula [III] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof.

cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone, etc. (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$ $^1$H-NMR (CDCl$_3$): δ 4.20 (1H, d, J=2.4 Hz, 5-H), 4.83 (1H,m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1.3, water)

UV: $\lambda_{max}$ 215 nm (water)

IR (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989–3991 (1969)] to determine the configuration.

Figure 7:
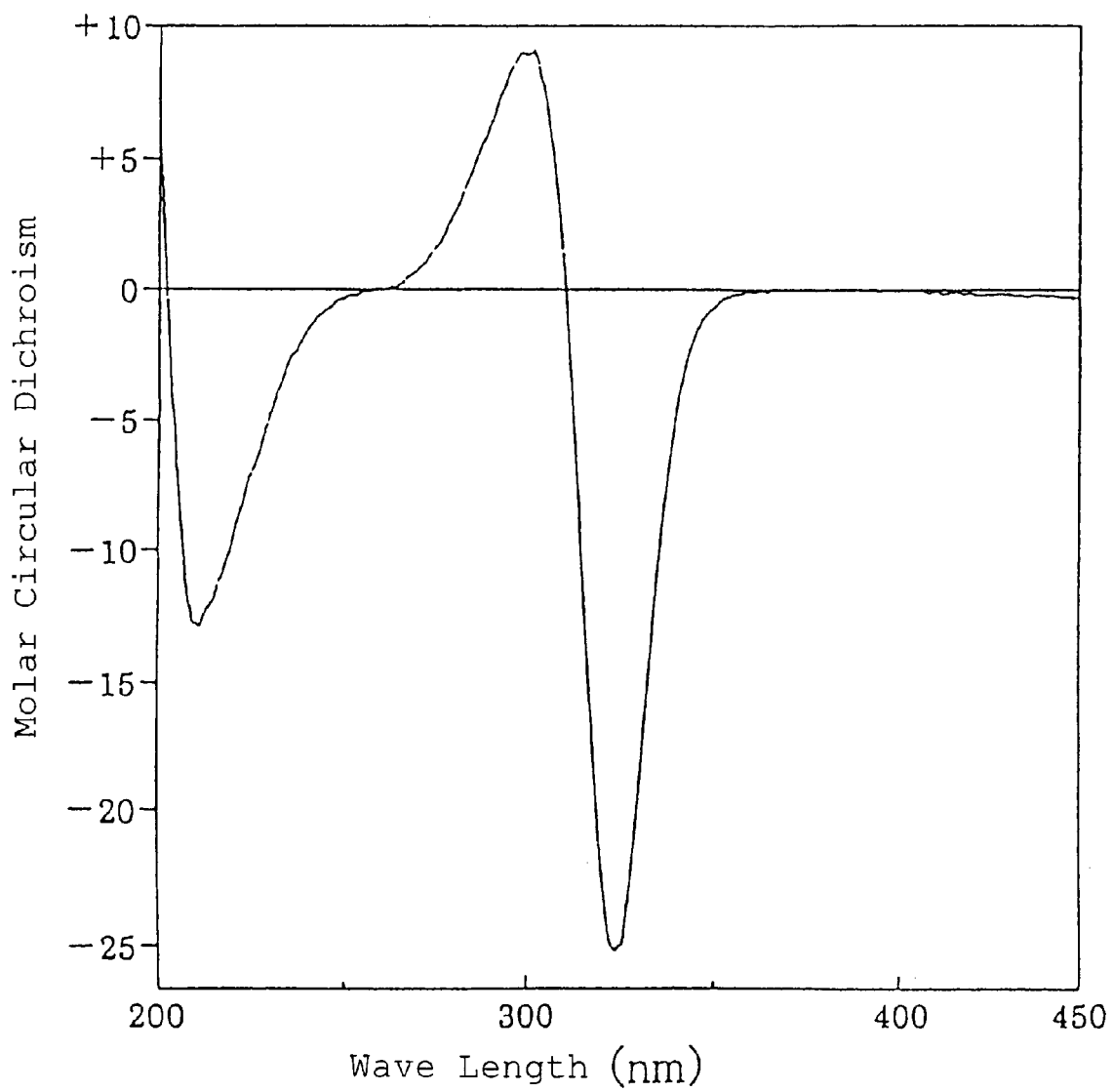
FIG. 7 shows a CD of p-dimethylaminobenzoyl derivative of (−)-cyclopentenone and a stereostructure of (−)-cyclopentenone.
Figure 7:
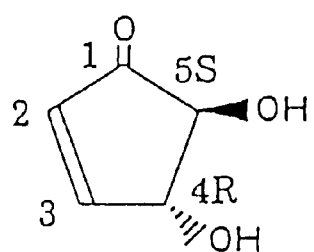

CD of p-dimethylaminobenzoyl derivative of (−)-cyclopentanone and stereostructure of (−)-cyclopentenone are shown in FIG. 7. In the drawing, the ordinate indicates molar circular dichroism while the abscissa indicates wave length (nm). Incidentally, the above stereostructure is given hereunder as the formula [IV]

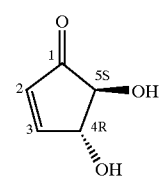

[IV]

Figure 8:
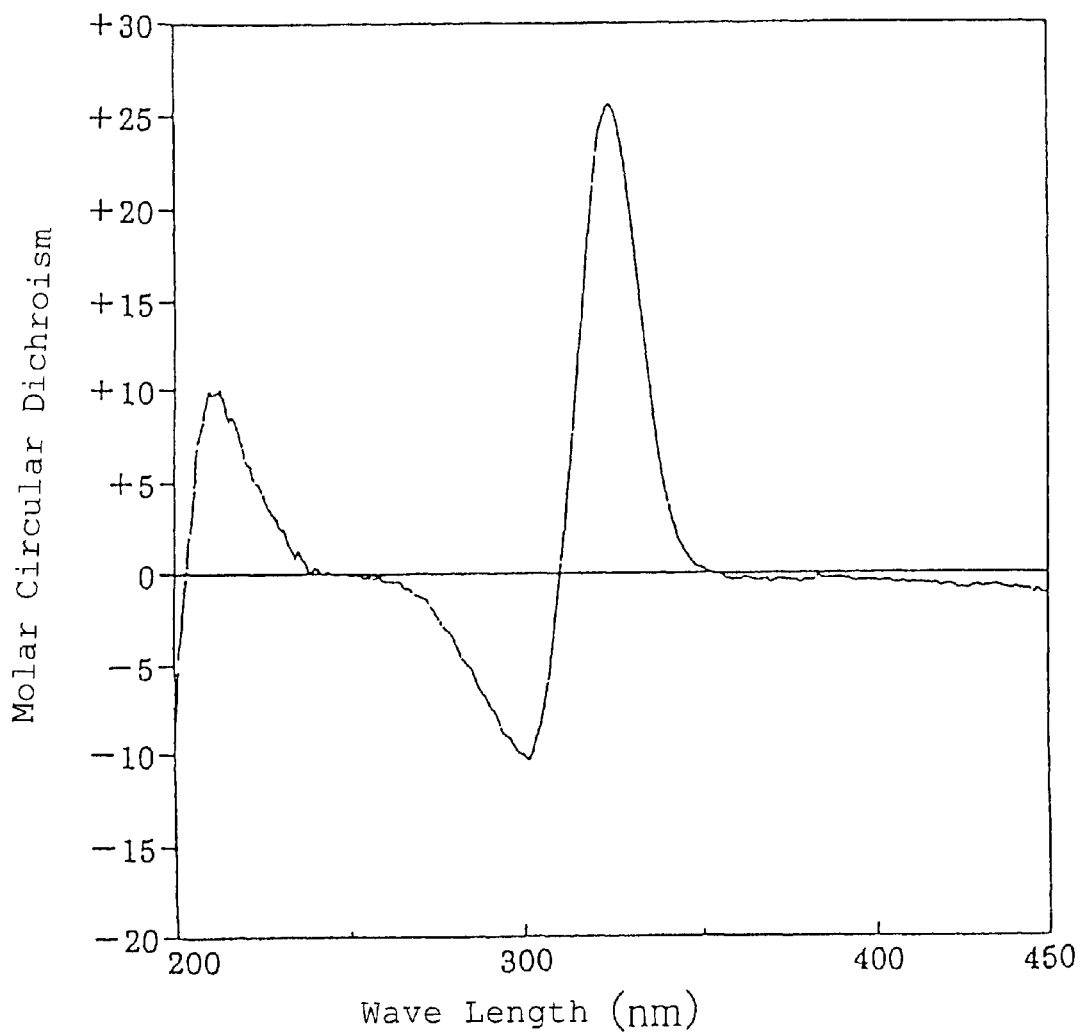
FIG. 8 shows a CD of p-dimethylaminobenzoyl derivative of (+)-cyclopentenone and a stereostructure of (+)-cyclopentenone.
Figure 8:
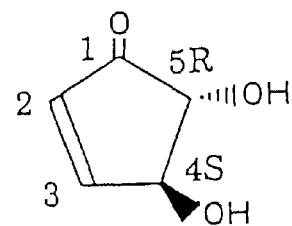

CD of p-dimethylaminobenzoyl derivative of (+)-cyclopentanone and stereostructure of (+)-cyclopentenone are shown in FIG. 8. In the drawing, the ordinate indicates molar circular dichroism while the abscissa indicates wave length (nm). Incidentally, the above stereostructure is given hereunder as the formula [V]

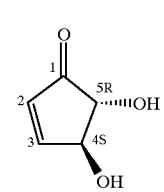

[V]

As shown in FIG. 7, FIG. 8, formula [IV] and formula [V], the (−)-cyclopentenone is (−)-(4R,5S)-trans-4,5-dihydroxy-2-cyclopenten-1-one while the (+)-cyclopentenone is (+)-(4S,5R)-trans-4,5-dihydroxy-2-cyclopenten-1-one.

The above-mentioned cyclopentenones or an optically active substance thereof maybe manufactured by any method, i.e. they may be manufactured by a method disclosed in this specification or by means of other chemical synthesis; and trans- and cis-cyclopentenone, a mixture thereof or optically active substances thereof may be used in the present invention as well.

When the cyclopentenone and/or an optically active substance thereof are/is made to react with alcohol and/or reactive derivative thereof having straight or branched alkyl group, straight or branched alkenyl group, aromatic group or aromatic-aliphatic group either simultaneously or successively, the cyclopentenone derivative of the present invention represented by the formula [II] or an optically active substance derivative thereof is produced in the reaction solution.

Alcohol having straight or branched alkyl group may be used as the alcohol having alkyl group and the length of the alkyl chain can be appropriately selected according to the biological activity, solubility, etc. of the cyclopentenone derivative.

Examples of the applicable alcohol having straight alkyl group are methanol, ethanol, propanol, butanol, pentanol, hexanol, heptanol, octanol, nonanol, decanol, lauryl alcohol, myristyl alcohol, palmityl alcohol and stearyl alcohol.

Examples of the applicable alcohol having branched alkyl group are isobutyl alcohol, tert-butyl alcohol, isoamyl alcohol and tert-amyl alcohol.

With regard to the alcohol having alkenyl group, alcohol having straight or branched alkenyl group may be used and the chain length, degree of unsaturation and position of the unsaturated bond of the alkenyl group may be appropriately selected according to biological activity, solubility, etc. of the cyclopentenone derivative.

Examples of the applicable alcohol having straight alkenyl group are vinyl alcohol, allyl alcohol, croton alcohol and 3-hexen-1-ol.

Examples of the applicable alcohol having branched alkenyl group are geraniol, farnesol, geranylgeraniol, retinol, linalool, nerolidol and nerol.

Examples of the applicable alcohol having aromatic group are phenol, cresol, nitrophenol, chlorophenol, bromophenol, catechol, resorcinol, hydroquinone and naphthol and an alcohol having appropriate aromatic group may be selected according to biological activity, solubility, etc. of the cyclopentenone derivative to be manufactured.

Examples of the applicable alcohol having aromatic-aliphatic group are benzyl alcohol, phenetyl alcohol, phenacyl alcohol, styrene glycol and phenylpropanol and an alcohol having appropriate aralkyl group may be selected according to biological activity, solubility, etc. of the cyclopentenone derivative to be manufactured.

Examples of the reactive derivative of alcohol used in the present invention are alkyl halides, aryl halides, acid esters, diazo compounds, salts and alkenes which are dehydrated products of alcohol and such a reactive derivative of alcohol which is to be used may be prepared depending upon the object.

Reaction of alcohol and/or reactive derivative thereof with cyclopentenone may be conducted so as to make $R_3$ and $R_4$ of the cyclopentenone derivative represented by the formula [II] same, to leave one of $R_3$ and $R_4$ unreacted H, or to make $R_3$ and $R_4$ different. Thus, the two hydroxyl groups of cyclopentenone may be made to react at the same time; one of them may be made to react; alcohol where $R_3$ and $R_4$ are different and/or a reactive derivative thereof may be made to react with cyclopentenone at the same time; or alcohol where $R_3$ and $R_4$ are different and/or a reactive derivative thereof may be made to react with cyclopentenone successively. When one of the hydroxyl groups of cyclopentenone is protected, it is possible to efficiently manufacture a cyclopentenone derivative where alcohol where $R_3$ and $R_4$ are different or a cyclopentenone derivative where one of $R_3$ and $R_4$ is etherified.

Incidentally, in the cyclopentenone derivative represented by the formula [I] offered by the present invention, $R_1$ and $R_2$ in said cyclopentenone derivative may be same, one of $R_1$ and $R_2$ therein may be unreacted H, or $R_1$ and $R_2$ therein may be different as well.

The cyclopentenone derivative or an optically active substance thereof which is produced by the reaction of the cyclopentenone or an optically active substance thereof with alcohol and/or reactive derivative thereof has a potent inhibiting activity for growth of oncogene and can be purified and isolated from the reaction solution using said activity as an index. The means for purification and isolation may be known purifying means such as chemical method and physical method. Thus, conventionally known methods such as gel filtration, fractionation using a molecular weight fractionating membrane, extraction with solvent, fractional distillation and various chromatographic methods using ion exchange, normal phase, reversed phase, etc. are combined whereby the cyclopetenone derivative or an optically active substance thereof can be purified and isolated.

For example, cyclopentenone or its optically active substance and trichloroacetimidate of benzyl alcohol or tert-butyl alcohol are dissolved in an argon stream and a solution of boron trifluoride-diethyl ether complex is added thereto and made to react therewith to give the cyclopentenone derivative of the present invention.

When cyclopentenone or its optically active substance is dissolved in tetrahydrofuran and then alkyl halide and sodium hydride are added thereto and made to react therewith, the cyclopentenone derivative of the present invention is produced.

When cyclopentenone or its optically active substance is dissolved in dioxane and then potassium hydroxide and dimethyl sulfate are added thereto and made to react therewith, the cyclopentenone derivative of the present invention is produced.

When cyclopentenone or its optically active substance is dissolved in dichloromethane and then diisopropyl ethylamine and triethyloxonium tetrafluoroborate are added thereto and made to react therewith, the cyclopentenone derivative of the present invention is produced.

Further, when cyclopentenone or its optically active substance is dissolved in dichloromethane and then trifluoromethanesulfonic acid and alkene are added thereto and made to react therewith, the cyclopentenone derivative of the present invention is produced.

The cyclopentenone derivative of the present invention which is produced as such may, if necessary, be purified and isolated by known means such as extraction with solvent, column chromatography and thin layer chromatography.

Separation of the optically active substances of the cyclopentenone derivative obtained by the present invention can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylate stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

With regard to the salt of the compound of the present invention or optically active substance thereof, salts which are acceptable as pharmaceutical agents are exemplified and they may be prepared by converting by means of known methods.

The cyclopentenone derivative represented by the formula [I] or [II] of the present invention (hereinafter, referred to as just "cyclopentenone derivative of the present invention"), an optically active substance thereof or a salt thereof has physiological activities such as anticancer activity, activity of growth inhibition of cancer cells, apoptosis-inducing activity, activity of topoisomerase II inhibition, induction activity of the cancer cell differentiation, antirheumatic activity, activity of chronic articular rheumatism inhibition, activity of inducing the Fas antigen production, antibacterial activity, antiviral activity, activity of improving the hepatic function, activity of inducing the heat shock protein, normalizing activity of the blood components, enhancer activity of the cancer immunity, anti-inflammation activity, inhibition activity of tumor necrosis factor expression, inhibition activity of nitrogen monoxide production, immunomodulating activity such as inhibition activity of delayed type hypersensitivity, inhibition activity of lymphocyte transformation, inhibition activity of mixed lymphocyte reaction, inhibition activity of IgE production and inhibition activity of carrageenan edema and, due to those activities, pharmaceutical agent containing as an effective component at least one compound which is selected from the cyclopentenone derivative of the present invention, an optically active substance thereof or a salt thereof is useful as a drug acting biophylaxic function such as pharmaceutical preparation acting the antibody production function, anti-inflammatory agent, antiallergic agent, antirheumatic agent and interferon inducer, a drug acting the saccharide metabolism such as remedy for diabetes mellitus and a drug acting the pathogenic organisms such as antibacterial agent and antiviral agent. Accordingly, the pharmaceutical agent obtained by the present invention is quite useful as a drug for the diseases which show sensitivity to the compound of the present invention, an optically active substance thereof or a salt thereof, i.e. as a drug for therapy or prevention of, for example, cancer, viral diseases, rheumatism, diabetes mellitus, allergy, autoimmune diseases, inflammation, etc.

The cyclopentenone derivative of the present invention, an optically active substance thereof or a salt thereof has a cell growth suppressing action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colon cancer cells HCT 116, human colon cancer cells SW 480, human colon cancer cells WiDr, stomach cancer cells AGS and myeloma cells. An anticancer agent can be prepared when at least one of the compound selected from the cyclopentenone derivative of the present invention, an optically active substance thereof or a salt thereof is used as an effective component and is made into a pharmaceutical preparation by compounding with known pharmaceutical carriers. Mechanism of anticancer activity of the cyclopentenone derivative, an optically active substance thereof or a salt thereof obtained by the present invention does not limit the scope of the present invention at all and, for example, an apoptosis inducing action and an activity of topoisomerase inhibition to cancer cells is covered by anticancer activity of the present invention as well.

Generally, the compound selected from the cyclopentenone derivative of the present invention, an optically active substance thereof or a salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where the compound selected from the cyclopentenone derivative of the present invention, an optically active substance thereof or a salt thereof which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated and it is not constant but, usually, the amount of the cyclopentenone derivative of the present invention, an optically active substance thereof or a salt thereof contained in the preparation is from 0.1 µg to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The cyclopentenone derivative of the present invention, an optically active substance or a salt thereof has an apoptosis inducing action. When an apoptosis inducer can be made into pharmaceutical preparations according to the above-mentioned anticancer agent, the apoptosis inducer containing at least one compound selected from the cyclopentenone derivative of the present invention, an optically active substance or a salt thereof as an effective component can be prepared and can be administered by the same manner as in the case of the anticancer agent.

The dose as the apoptosis inducers is not particularly specified but may be appropriately determined depending upon the dosage form, administration method, purpose of the use and age, body weight, conditions, etc. of the patient to whom the inducer is administered. Usually, however, the amount of the compound selected from the cyclopentenone derivative of the present invention, an optically active substance or a salt thereof contained in the preparation for an adult is 0.1 $\mu$g-100 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Unlike necrosis which is a pathogenic death of cells, apoptosis is a death which is initially programmed in the gene of the cell itself. Thus, the gene which programs the apoptosis is activated by certain external or internal causes whereby programmed cell death gene protein is produced or, in some case, programmed death protein which exists in cells as non-activated type is activated. Then the cell itself is decomposed and is believed to be dead by the resulting programmed death protein. The apoptosis inducer of the present invention is quite useful since it is capable of induction of such apoptosis in desired tissues and cells and able to exclude the unnecessary cells or the harmful cells from living organisms in a natural state.

Thus, the apoptosis inducer of the present invention is effective in elimination of, for example, virus-infected cells, cancer cells and autoreactive lymphocytes in the patients suffering from autoimmune diseases and, as a result of expression of apoptosis in desired tissues or cells, it is now possible to eliminate the unnecessary or harmful cells from living body in their natural form. Examples of the diseases for which the apoptosis inducer of the present invention is effective are systemic lupus erythematosus, immune-intervening glomerular nephritis, multiple sclerosis, collagen disease and other autoimmune diseases as well as rheumatism.

The apoptosis inducer of the present invention can be used in a method for the induction of apoptosis. Thus, when the cyclopentenone derivative of the present invention, an optically active substance thereof or a salt thereof is used as an effective component, it is possible to induce apoptosis and said method is useful, for example, for elucidation of a mechanism for apoptosis induction and for screening of apoptosis inducers and apoptosis induction inhibitors.

Carrageenan pododema model is a reaction in which carrageenan which is an inflammation inducer is subcutaneously injected to paws to induce inflammation cells such as macrophage and neutrophils whereby blood vessel permeability is enhanced by inflammatory factors produced from those cells inducing the edema. The inhibiting action of the above-mentioned immunomodulator to edema is useful for therapy or prevention of diseases requiring control of enhancement of blood vessel permeability such as chronic articular rheumatism. The cyclopentenone derivative of the present invention, an optically active substance thereof or a salt thereof has a suppressing action to edema caused by carrageenan and the pharmaceutical agents which contain at least one compound selected from those compounds as an effective component are useful as anti-inflammatory agents and antirheumatic agents which are useful for therapy or prevention of inflammatory diseases requiring the control of acceleration of permeability of blood vessels such as rheumatoid arthritis.

The present invention further offers a topoisomerase inhibitor containing at least one compound selected from the cyclopentenone derivatives of the present invention, optically active substances thereof or salts thereof as an effective component and also offers a method for the inhibition of topoisomerase where at least one compound selected from those compounds is used as an effective component. Such a topoisomerase inhibitor is useful as an anticancer agent while said topoisomerase inhibiting method is useful in biochemical studies and in screening of anticaner agents.

Furthermore, the present invention offers the pharmaceutical agents acting the biophylaxic mechanism such as preparations acting the anibody production mechanism, anti-inflammatory agents, antiallergic agents, antirheumatic agents, interferon inducers, etc., the pharmaceutical agents acting the saccharide metabolism such as remedies for diabetes mellitus, the pharmaceutical agents acting the pathogenic organisms such as antibacterial agents, antiviral agents, etc. and topoisomerase inhibitors and the like containing at least one compound selected from the cyclopentenone derivatives of the present invention, optically active substances thereof or salts thereof as an effective component and said pharmaceutical agents can be made into pharmaceutical preparations by the same manner as in the case of anticancer agents and can be administered in a method and dose by the same manner as in the case of anticancer agents.

The cyclopentenone derivative of the present invention, an optically active substance thereof or a salt thereof can be efficiently manufactured from cyclopentenone and any of desired alcohols or reactive derivatives thereof and the present invention offers the cyclopentenone derivative represented by the formula [II], an optically active substance thereof or a salt thereof.

There is no particular limitation for the method of manufacturing the food and beverage containing the cyclopentenone derivative, an optically active substance or a salt thereof obtained by the present invention but cooking, processing and commonly-used manufacturing methods for food and beverage may be applied provided that an effective amount of the cyclopentenone derivative of the present invention, an optically active substance or a salt thereof is contained in the resulting food or beverage.

The cyclopentenone derivative of the present invention, an optically active substance thereof or a salt thereof does not exhibit toxicity upon administration of its dose which is effective for achieving the physiological activity. For example, in the case of oral administration, no dead case was noted in mice by a single oral administration of 300 mg/kg of 4-tert-butylcyclopentenone ether, optically active substance or a salt thereof, or 4,5-di-tert-butylcyclopentenone ether, optically active substance or a salt thereof.

To sum up, the cyclopentenone derivative of the present invention, an optically active substance or a salt thereof can be easily manufactured and, due to its various physiological functions, it is a compound which is quite useful in broad areas of pharmaceutical agents, foods, etc.

EXAMPLES

The present invention will be further illustrated by way of the following examples although the present invention is never limited to those examples. Incidentally, "%" used in the examples stands for "% by weight".

Example 1

(1) D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column (manufactured by Takara Shuzo) and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This was filtered through a filter of 0.5 μm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 μl (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

(2) Cyclopentenone (44 mg) and 492 mg of benzyl 2,2,2-trichloroacetimidate (manufactured by Aldrich; 14,033-3) were dissolved in 2.5 ml of dichloromethane (manufactured by Wako Pure Chemical; 135-02441) in an argon stream. To this was gradually added a solution of 28 μl/ml boron trifluoride-diethyl ether complex (manufactured by Wako Pure Chemical; 022-08362) in 1 ml of dichloromethane with stirring. After stirring at room temperature for eight hours, the mixture was concentrated in vacuo followed by subjecting to a silica gel thin layer chromatography using chloroform:methanol (19:1) as a developer to purify 4-benzylcyclopentenone ether, 5-benzylcyclopentenone ether and 4,5-dibenzylcyclopentenone ether. The Rf values of 4-benzylcyclopentenone ether, 5-benzylcyclopentenone ether and 4,5-dibenzylcyclopentenone ether were 0.3, 0.45 and 0.8, respectively. Yields of 4-benzylcyclopentenone ether, 5-benzylcyclopentenone ether and 4,5-dibenzylcyclopentenone ether were 3.7%, 3.7% and 2.5%, respectively.

(3) Structures of 4-benzylcyclopentenone ether, 5-benzylcyclopentenone ether and 4,5-dibenzylcyclopentenone ether manufactured in Example 1-(2) were confirmed by means of a nuclear magnetic resonance (NMR). The apparatus used for the nuclear magnetic resonance was JNM-EX270 FT NMR System (manufactured by Nippon Denshi). Chemical shift values by $^1$H-NMR are given where that of tetramethylsilane is defined as 0 ppm. The result is given below.

4-Benzylcyclopentenone ether $^1$H-NMR: δ 7.47 (1H, dd, J=6.0 Hz, J=1.68) , δ 7.36 (5H, m), δ 6.3 (1H, dd, J=6.0 Hz, J=1.33 Hz), δ 4.88 (1H, d, J=11.55), δ 4.75 (1H, d, J=11.55), δ 4.55 (1H, m), δ 4.28 (1H, m), δ 2.78 (1H, m)

5-Benzylcyclopentenone ether $^1$H-NMR: δ 7.39 (6H, m), δ 6.22 (1H, dd, J=6.24 Hz, J=1.32 Hz), δ 5.09 (1H, d, J=11.87), δ 4.79 (1H, m), δ 4.77 (1H, d, J=11.87), δ 3.98 (1H, d, J=2.97), δ 2.06 (1H, m)

4,5-Benzylcyclopentenone ether $^1$H-NMR: δ 7.47 (1H, dd, J=6.27 Hz, J=1.98), δ 7.34 (10H, m), δ 6.29 (1H, dd, J=6.10 Hz, J=1.49 Hz), δ 4.88 (1H, d, J=11.85), δ 4.74 (1H, d, J=11.85), δ 4.71 (2H, d, J=11.55), δ 4.56 (1H, m), δ 4.33 (1H, d, J=2.64)

Figure 2:
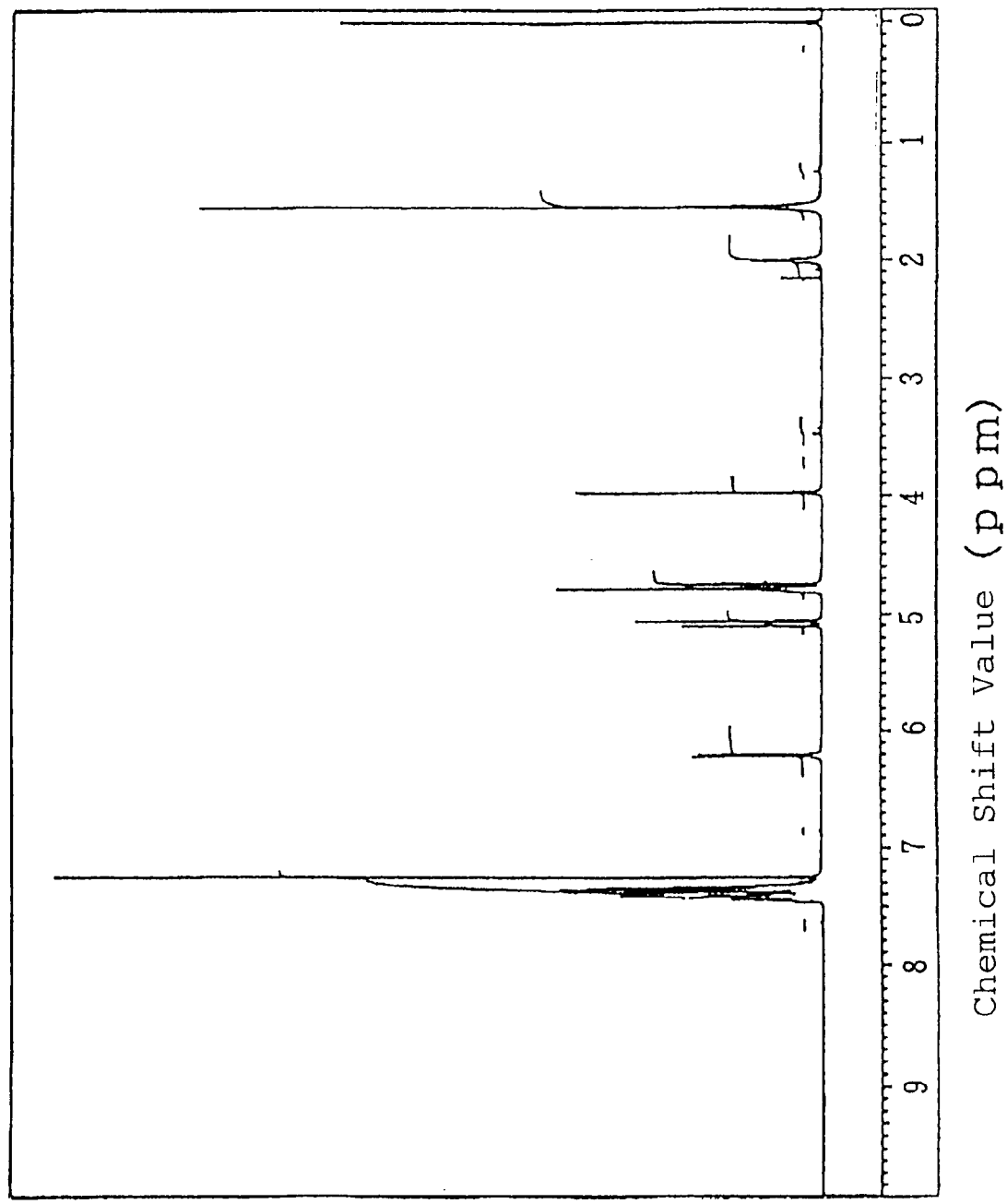
FIG. 2 shows a $^1$H-NMR spectrum of 5-benzylcyclopentenone ether.
Figure 3:
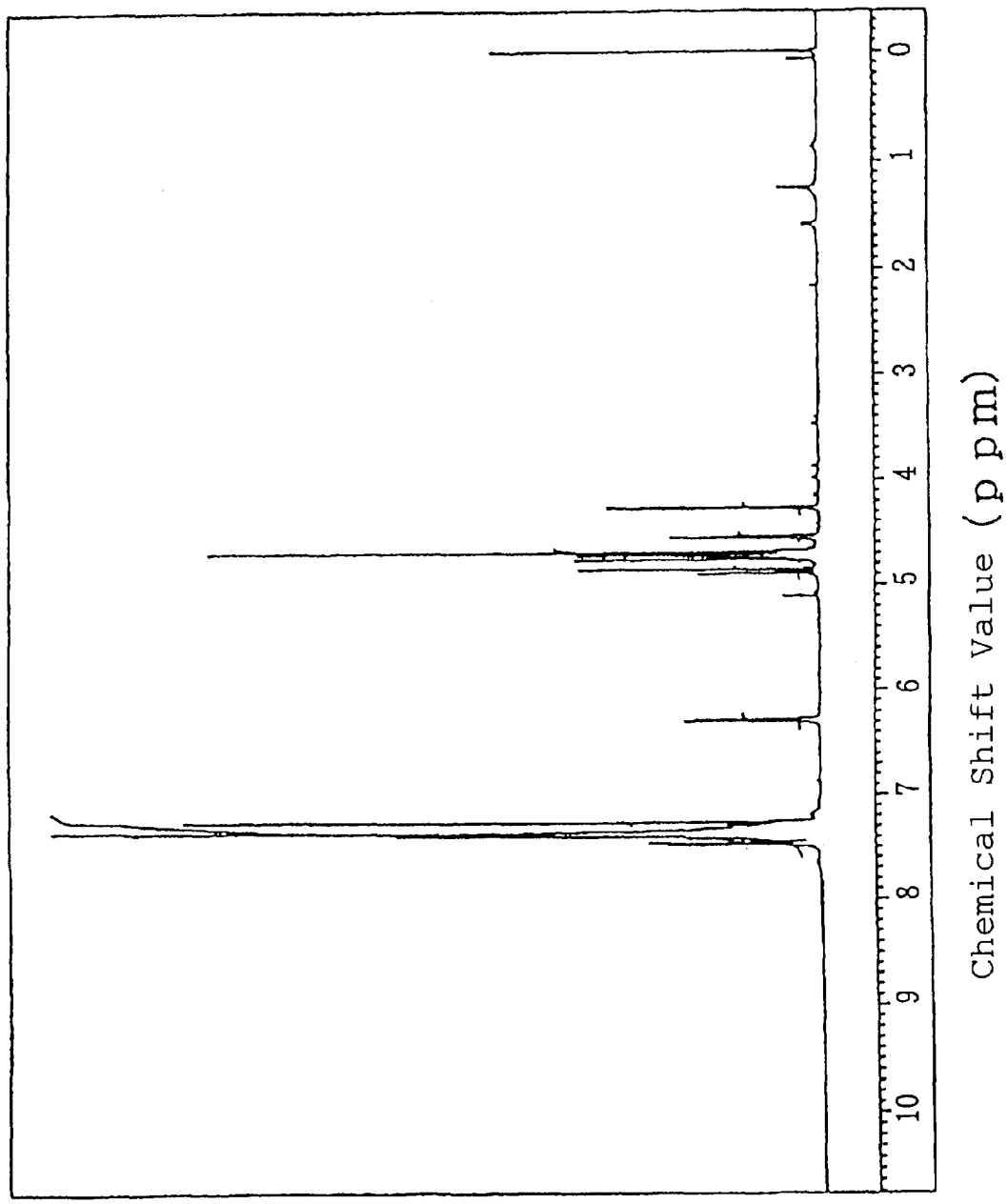
FIG. 3 shows a $^1$H-NMR spectrum of 4,5-dibenzylcyclopentenone ether.

$^1$H-NMR spectra of those derivatives are shown in FIG. 1 to FIG. 3. Thus, FIG. 1 shows an NMR spectrum of 4-benzylcyclopentenone ether, FIG. 2 shows an NMR spectrum of 5-benzylcyclopentenone ether and FIG. 3 shows an NMR spectrum of 4,5-dibenzylcyclopentenone ether. In FIG. 1 to FIG. 3, the abscissa indicates chemical shift values (ppm) and the ordinate indicates signal intensity.

(4) Cyclopentenone (44 mg) and 287 mg of tert-butyl 2,2,2-trichloroacetimidate (manufactured by Aldrich, 36,478-9) were dissolved in 2.5 ml of dichloromethane in an argon stream. To this was gradually added 1 ml of a solution of 28 μl/ml of boron trifluoride-diethyl ether complex in dichloromethane with stirring. The mixture was stirred at room temperature for eight hors, concentrated in vacuo and subjected to a silica gel thin layer chromatography by the same manner as in Example 1- (2) to purify 4-tert-butylcyclopentenone ether, 5-tert-butylcyclopentenone ether and 4,5-di-tert-butylcyclopentenone ether. The Rf values of 4-tert-butylcyclopentenone ether, 5-tert-butylcyclopentenone ether and 4,5-di-tert-butylcyclopentenone ether were 0.35, 0.27 and 0.73, respectively. Yields of 4-tert-butylcyclopentenone ether, 5-tert-butylcyclopentenone ether and 4,5-di-tert-butylcyclopentenone ether were 9.2%, 1.9% and 11%, respectively.

(5) Structures of 4-tert-butylcyclopentenone ether, 5-tert-butylcyclopentenone ether and 4,5-di-tert-butylcyclopentenone ether manufactured in Example 1-(4) were confirmed by means of an NMR in the same manner as in Example 1-(3). The result is shown below.

4-tert-Butylcyclopentenone ether $^1$H-NMR: δ 7.34 (1H, dd, J=5.94 Hz, J=0.99), δ 6.25 (1H, J=6.10, J=1.49), δ 4.59 (1H, m), δ 4.08 (1H, d, J=2.31), δ 2.85 (1H, m), δ 1.33 (9H, s)

5-tert-Butylcyclopentenone ether $^1$H-NMR: δ 7.37 (1H, dd, J=6.27 Hz, J=1.98), δ 6.23 (1H, J=6.27, J=1.32), δ 4.75 (1H, m), δ 4.04 (1H, d, J=2.63), δ 2.23 (1H, m), δ 1.32 (9H, s)

4,5-di-tert-Butylcyclopentenone ether $^1$H-NMR: δ 7.35 (1H, dd, J=6.27 Hz, J=1.65), δ 6.24 (1H, J=6.26, J=0.99), δ 4.62 (1H, ddd, J=3.3, J=1.65, J=0.99), δ 4.16 (1H, d, J=3.31), δ 1.38 (18H, s)

Figure 4:
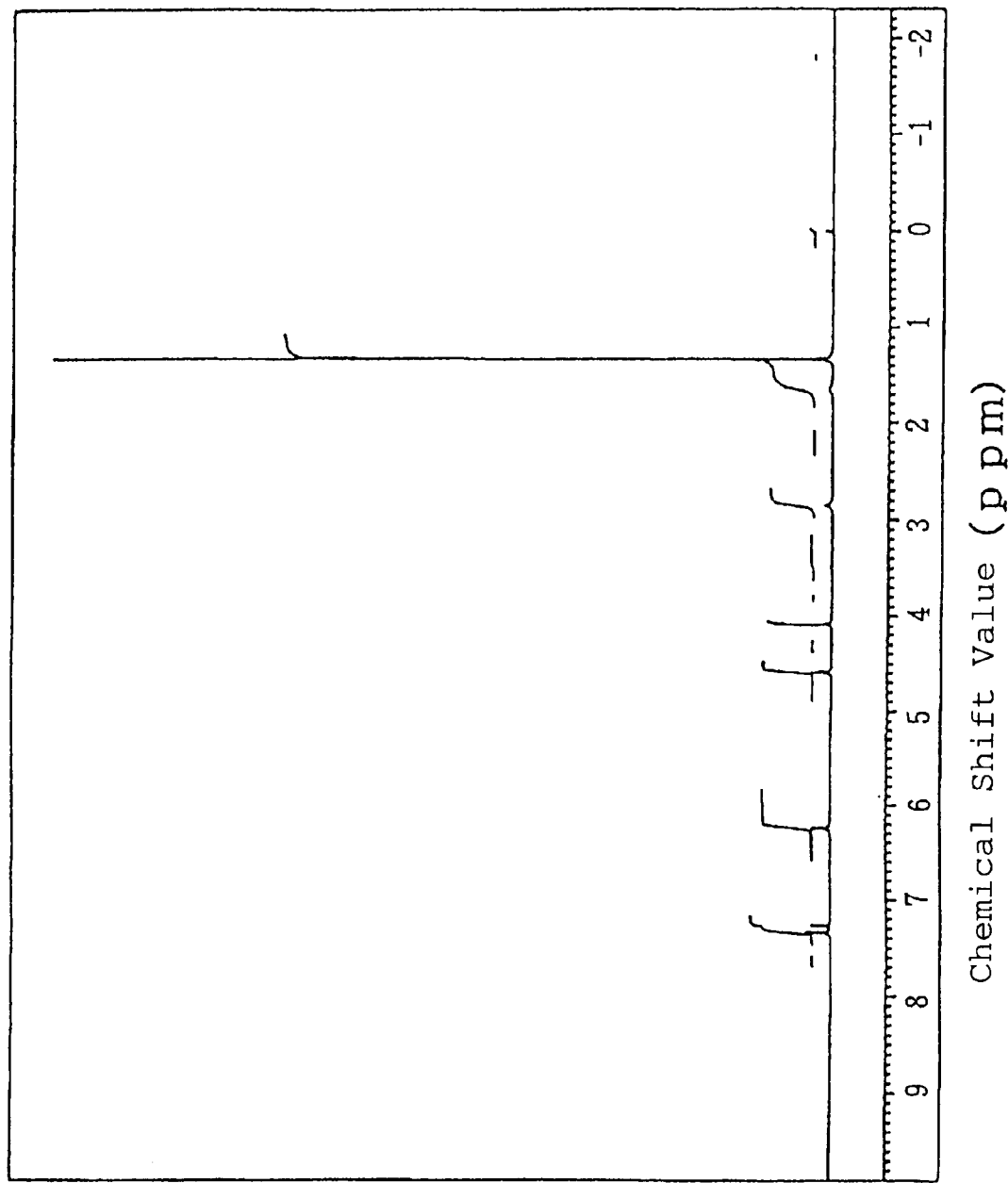
FIG. 4 shows a $^1$H-NMR spectrum of 4-tert-butylcyclopentenone ether.
Figure 5:
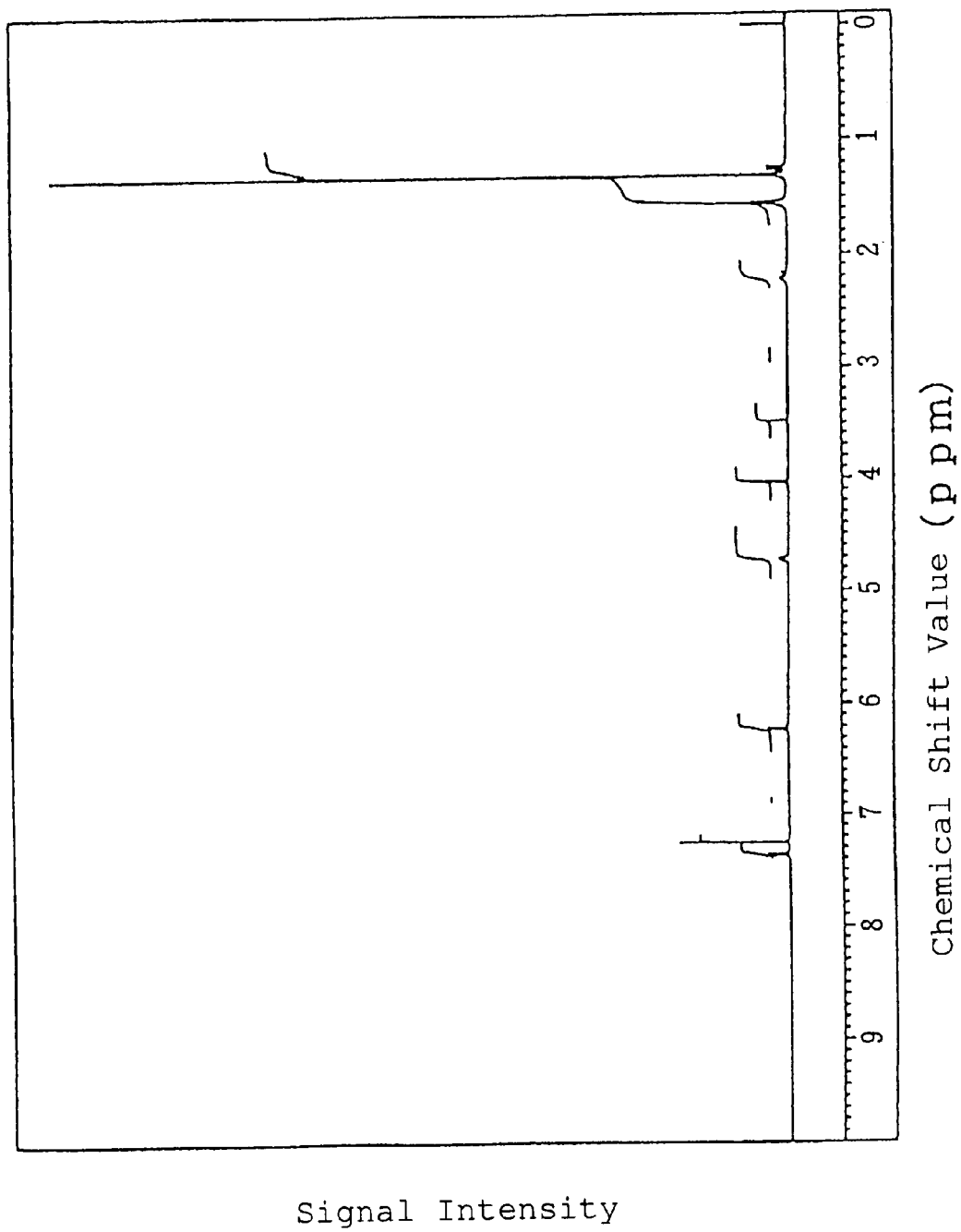
FIG. 5 shows a $^1$H-NMR spectrum of 5-tert-butylcyclopentenone ether.
Figure 6:
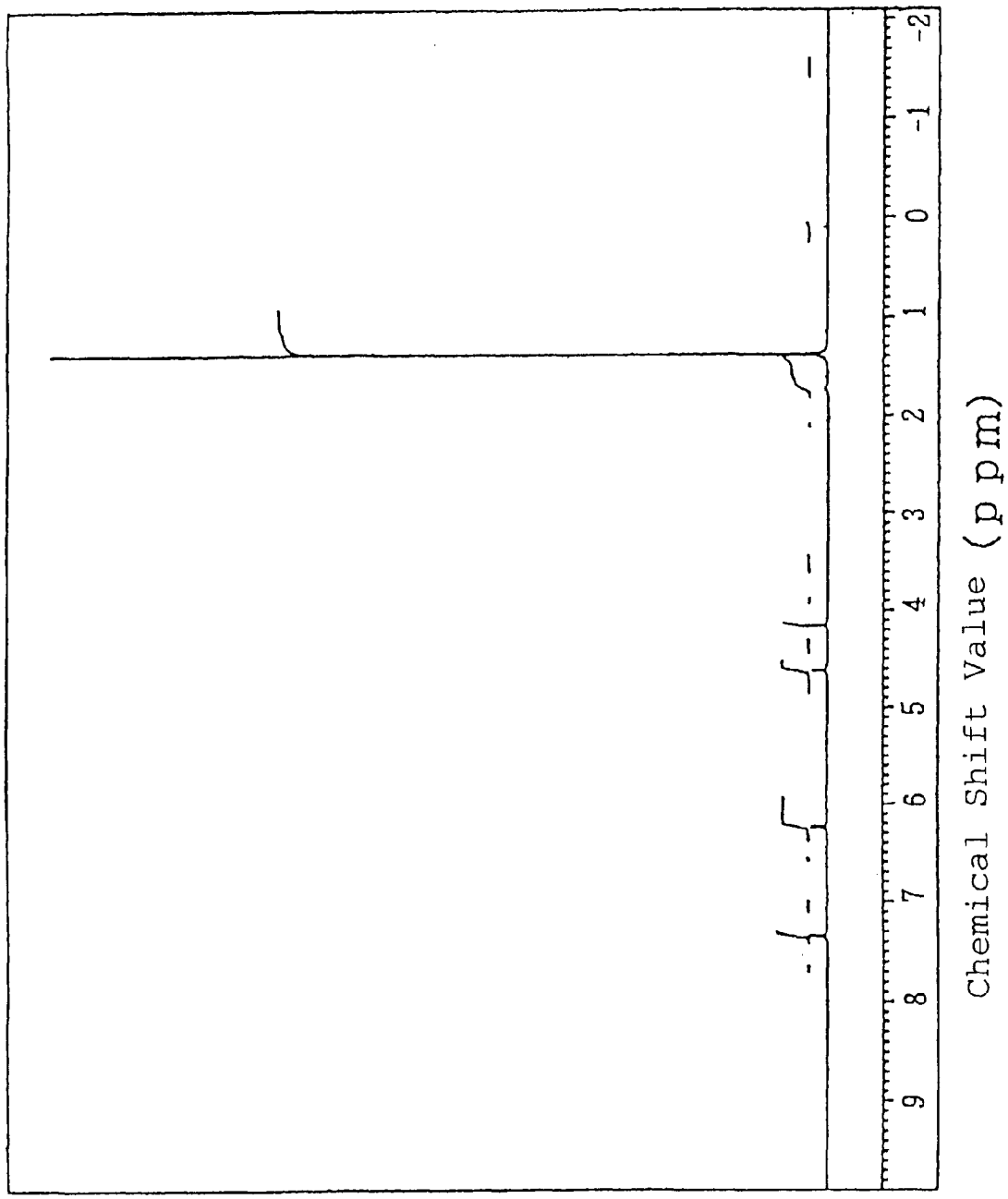
FIG. 6 shows a $^1$H-NMR spectrum of 4,5-di-tert-butylcyclopentenone ether.

$^1$H-NMR spectra of those derivatives are shown in FIG. 4 to FIG. 6. Thus, FIG. 4 shows an NMR spectrum of 4-tert-tylcyclopentenone ether, FIG. 5 shows an NMR spectrum of 5-tert-butylcyclopentenone ether and FIG. 6 shows an NMR spectrum of 4,5-di-tert-butylcyclopentenone ether. In FIG. 4 to FIG. 6, the abscissa indicates chemical shift values (ppm) and the ordinate indicates signal intensity.

Example 2

(1) A 1.22, 2.44, 4.88, 9.77, 19.5, 39.1, 78.1, 156, 313, 625, 1250, 2500, 5000 or 10000 μg/ml solution (10 μl) (in 70% aqueous solution of ethanol) of 4-benzylcyclopentenone ether, 5-benzylcyclopentenone ether or 4,5-dibenzylcyclopentenone ether or a 70% aqueous solution of ethanol as a control (10 μl) was added to each well of a 96-well microtiter plate followed by drying with air. Promyelocytic leukemia cell strain HL-60 (ATCC CCL-240) was suspended in an RPMI 1640 medium containing 10% of fetal calf serum to an extent of 1×10$^5$ cells/ml, each 100 μl thereof was poured into each well of the above microtiter plate and incubated at 37° C. for 48 hours in the presence of 5% of CO$_2$. Incubation was continued for four hours more after addition of 10 μl of a solution (5 mg/ml) of 3-(4,5-dimethylthiazol-2-yl)-2,5-diphenyltetrazolium bromide (MTT; manufactured by Sigma) in a phosphate-buffered aqueous saline solution and then the state of growth of the cells was observed under a microscope. Further, 100 μl of 2-propanol containing 0.04N HCl was added thereto followed by well stirring and the absorbance at 590 nm was measured.

The result was that the growth of the cells was completely suppressed in the section to which 2.44 μg/ml of 4-benzylcyclopentenone ether (final concentration: 0.244 μg/ml; 1.20 μM), 19.5 μg/ml of 5-benzylcyclopentenone ether (final concentration: 1.95 μg/ml; 9.56 μM) or 156 μg/ml of 4,5-dibenzylcyclopentenone ether (final concentration: 15.6 μg/ml; 53.1 μM) was added. Formation of apoptic body was noted as well. Incidentally, in the sections to which lower concentrations than the above were added, there was no difference between them and the water-added control section.

(2) Influence of 4-tert-butylcyclopentenone ether, 5-tert-butylcyclopentenone ether or 4,5-di-tert-butylcyclopentenone ether to the growth of HL-60 cells was measured by the same method as in Example 2-(1).

The result was that the growth of the cells was completely suppressed in the section to which 313 μg/ml of 4-benzylcyclopentenone ether (final concentration: 31.3 μg/ml; 180 μM), 78.1 μg/ml of 5-benzylcyclopentenone ether (final concentration: 7.81 μg/ml; 46 μM) or 625 μg/ml of 4,5-dibenzylcyclopentenone ether (final concentration: 62.5 μg/ml; 280 μM) was added. Formation of apoptic body was noted as well. Incidentally, in the sections to which lower concentrations than the above were added, there was no difference between them and the water-added control section.

In the meanwhile, the above-mentioned compounds showed an activity of suppressing the cancer cell growth and an activity of apoptosis induction. Optically active substances of those compounds showed both activities to a similar extent.

Example 3

Lewis rats (male; nine weeks age; body weight: about 250 g) were purchased from Seakku-Yoshitomi and the inflammation models such as carrageenan-induced pedal edema model (a model of rheumatoid arthritis) were prepared as follows whereby the tested substances were evaluated.

Thus, 4-tert-butylcyclopentenone ether or 4,5-di-tert-butylcyclopentenone ether in various concentrations by dissolving in olive oil (manufactured by Nacalai Tesque) was orally administered at the dose of 1 mg/10 ml/kg or 10 mg/10 ml/kg to rats which were fasted for 18 hours before initiation of the experiment.

After 0.5 hour from administration of these test drugs, 100 μl/rat of 1% suspension of carrageenan (manufactured by Wako) in a physiologically saline solution (manufactured by Otsuka Pharmaceutical) was injected to right paw to induce pedal edema. After three hours from the carrageenan injection, volume of right paw of the rat was measured by a pedal volume measuring device (manufactured by UGO BASILE). Incidentally, the measured value was expressed by calculating the increasing rate from the right paw volume of each rat measured before the carrageenan administration.

Figure 9:
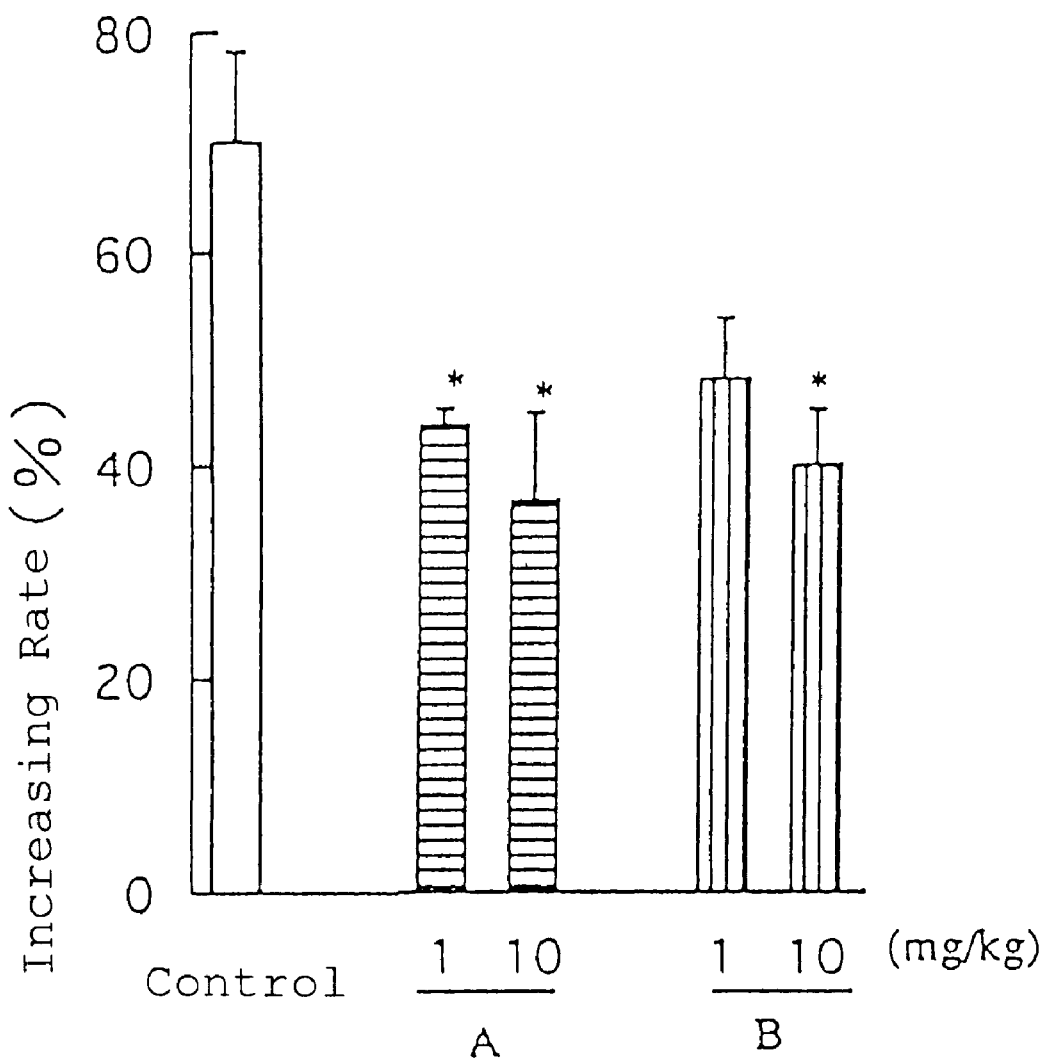
FIG. 9 shows a relation between the amount of 4-tert-butylcyclopentenone ether or 4,5-di-tert-butylcyclopentenone ether and the increasing rate of the pedal edema.

The result is shown in FIG. 9. Thus, FIG. 9 shows the relation between the amount of each compound and the increasing rate of the pedal edema in which ordinate indicates an increasing rate (%) while abscissa indicates a dose of each conpound (mg/kg).

In FIG. 9, A is a group to which 4-tert-butylcyclopentenone ether was administered while B is a group to which 4,5-di-tert-butylcyclopentenone ether was administered. Each of the compounds showed an suppressing action to edema induced by carrageenan. Incidentally, * in FIG. 9 means that it is significantly different from the control group at p<0.05.

Other cyclopentenone derivatives of the present invention prepared in Example 1 also showed the suppressing action to carrageenan edema to the same extent as the above compounds did.

Example 4

(1) One μl of 0.25 μg/μl pBR322 DNA (manufactured by Takara Shuzo) was added to a mixture of 2 μl of topoisomerase II (manufactured by TopoGEN, 2 units/μl), 2 μl of a buffer with a ten-fold diluted concentration [0.5M Tris-HCl (pH 8.0), 1.2M KCl, 0.1M $MgCl_2$, 5 mM adenosine triphosphate and 5 mM dithiothreitol], 2 μl of 0.1% bovine serum albumin (manufactured by Takara Shuzo), 11 μl of distilled water and 2 μl of distilled water (a control) or 4,5-di-tert-butylcyclopentenone ether prepared into various concentrations by water and made to react at 37° C. After the reaction for 30 minutes, the reaction was stopped by adding 2 μl aqueous solution of 1% sodium dodecylsulfate, 50% glycerol and 0.02% Bromophenol Blue.

The above reaction solution (20 μl) was applied to 1% agarose gel prepared from agarose L03 (manufactured by Takara Shuzo) and TAE buffer [40 mM Tris, 5mM sodium acetate and 1 mM disodium ethylenediaminetetraacetate (EDTA); adjusted to pH 7.8 with acetic acid] and electrophoresis was conducted in the TAE buffer. After the electrophoresis, the gel was dipped in an aqueous solution of 1 μg/ml ethidium bromide and irradiated with ultraviolet ray to observe the electrophoretic pattern of DNA. In a control which was an aqueous solution, DNA completely changed from a supercoiled type to a relaxation type but, when topoisomerase II activity was inhibited, the change from a supercoild type to a relaxation type was partially or completely inhibited.

The result was that 4,5-di-tert-butylcyclopentenone ether showed a topoisomerase suppressing activity at the concentration of not less than 250 μM in the reaction solution. Thus, the superhelix DNA remained to an medium extent by 250 μM, most of the superhelix DNA remained by 500 μM, and the superhelix DNA did not decrease at all by 1000 μM. Optically active substances of 4,5-di-tert-butylcyclopentenone ether and other compounds of the present invention prepared in Example 1 including their optically active substances showed the same activity as well.

As such, the compounds of the present invention showed a suppressing activity to topoisomerase II which is temporarily expressed only in a divisional stage in normal cells and is highly expressed during all of cellular period as a result of canceration of the cells.

Example 5

Injection Preparations (1) 4-benzylcyclopentenone ether or 5-benzylcyclopentenone ether was added to a physiological saline solution (as listed in the Japanese Pharmacopoeia) in a concentration of 1% to prepare an injection preparation.

(2) 4-benzylcyclopentenone ether or 5-benzylcyclopentenone ether, and glycyrrhizic acid were added to a physiological saline solution (the same as above) in concentrations of 0.5% and 0.1%, respectively, to prepare an injection preparation.

Example 6

Tablets (1) A tablet containing 100 mg of 4-benzylcyclopentenone ether and an appropriate amount of microcrystalline cellulose was prepared and coated with sugar to manufacture a tablet preparation.

(2) A tablet containing 0.1 mg of 5-benzylcyclopentenone ether, 10 mg of dipotassium glycyrrhizinate and an appropriate amount of microcrystalline cellulose was prepared and coated with sugar to manufacture a tablet preparation.

MERIT OF THE INVENTION

The present invention offers the manufacturing method for the cyclopentenone derivative, an optically active substance thereof or a salt thereof which exhibits the physiological activities such as anticancer activity, cell growth inhibiting activity on cancer cells, apoptosis induction activity, etc. The pharmaceutical agent using the compound offered by the present invention as an effective component is a useful pharmaceutical agent especially for keeping homeostatis of living body.

What is claimed is:

1. A cyclopentenone derivative represented by the following formula I or an optically active substance or a salt thereof;

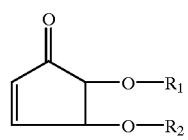

I wherein $R_1$ and $R_2$ are same or different and each of them is straight or branched alkyl group, straight or branched alkenyl group, aromatic group, aromatic-aliphatic group or H with a proviso that the case where $R_1=R_2=H$, $R_1=R_2=$benzyl group, $R_1=H$ and $R_2=$alkyl group or $R_1=$benzyl group and $R_2=H$ is excluded.

2. A method for the manufacture of a cyclopentenone derivative represented by the formula II, characterized in that 4,5-dihydroxy-2-cyclopenten-1-one represented by the following formula III and/or an optically active derivative thereof are/is made to react with alcohol and/or a reactive derivative thereof corresponding to $R_3$ and $R_4$ of the cyclopentenone derivative represented by the following formula II either simultaneously or successively;

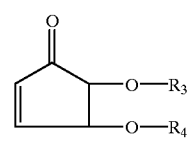

II wherein $R_3$ and $R_4$ are same or different and each of them is straight or branched alkyl group, straight or branched alkenyl group, aromatic group, aromatic-aliphatic group or H with a proviso that the case where $R_3=R_4=H$ is excluded.

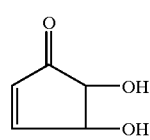

III

3. A pharmaceutical agent which is characterized in containing at least one compound selected from the cyclopentenone derivative, an optically active substance or a salt thereof as an effective component, wherein the cyclopentenone derivative is represented by the following formula I;

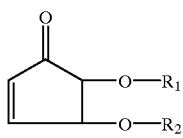

I wherein $R_1$ and $R_2$ are the same or different and each of them is straight or branched alkyl group, straight or branched alkenyl group, aromatic group, aromatic-aliphatic group or H with a proviso that the case where $R_1$ and $R_2$=H, $R_1$ and $R_2$ benzyl group, or $R_1$-benzyl group and $R_2$=H is excluded.

4. A pharmaceutical agent according to claim 3 which the agent is an anticancer agent.

5. A pharmaceutical agent according to claim 3 which the agent is an apoptosis-inducing agent.

6. A pharmaceutical agent which is characterized in containing at least one compound selected from the cyclopentenone derivative, an optically active substance or a salt thereof obtained by the method according to claim 2 as an effective component.

7. A pharmaceutical agent according to claim 6 which the agent is an anticancer agent.

8. A pharmaceutical agent according to claim 6 which the agent is an apoptosis inducing agent.

* * * * *

UNITED STATES PATENT AND TRADEMARK OFFICE
CERTIFICATE OF CORRECTION

PATENT NO : 6,111,145
DATED : August 29, 2000
INVENTOR(S): Eiji Kobayashi et al.

It is certified that error appears in the above-identified patent and that said Letters Patent is hereby corrected as shown below:

[22] PCT Filed:      June 5, 1998

[86] PCT No.:        PCT/JP98/02516

§ 371 Date:     October 15, 1999

§ 102(e) Date:  October 15, 1999

[87] PCT Pub. No.:   WO99/00349

PCT Pub. Date:  January 7, 1999

Signed and Sealed this

Fifteenth Day of May, 2001

Attest:

NICHOLAS P. GODICI

Attesting Officer    Acting Director of the United States Patent and Trademark Office